(12) United States Patent
Brahm

(10) Patent No.: US 9,795,638 B1
(45) Date of Patent: Oct. 24, 2017

(54) CARDIOTHORACIC CONSTRUCT AND METHODS OF USE

(71) Applicant: BioDlogics, LLC, Cordova, TN (US)

(72) Inventor: Timothy R. Brahm, Germantown, TN (US)

(73) Assignee: BioDLogics, LLC, Cordova, TN (US)

( * ) Notice: Subject to any disclaimer, the term of this patent is extended or adjusted under 35 U.S.C. 154(b) by 0 days.

(21) Appl. No.: 14/210,514

(22) Filed: Mar. 14, 2014

Related U.S. Application Data

(60) Provisional application No. 61/802,439, filed on Mar. 16, 2013.

(51) Int. Cl.
| | | |
|---|---|---|
| C12N 5/00 | (2006.01) | |
| C12N 5/02 | (2006.01) | |
| A61F 2/00 | (2006.01) | |
| A61K 35/50 | (2015.01) | |

(52) U.S. Cl.
CPC .................................. *A61K 35/50* (2013.01)

(58) Field of Classification Search
CPC ....................................................... A61K 35/50
USPC ................................................. 424/582, 583
See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,131,907 A * | 7/1992 | Williams | A61L 27/34 424/93.7 |
| 5,607,590 A | 3/1997 | Shimizu | |
| 5,618,312 A | 4/1997 | Yui | |
| 6,152,142 A | 11/2000 | Tseng | |
| 6,254,637 B1 | 7/2001 | Lee | |
| 6,326,019 B1 | 12/2001 | Tseng | |
| 6,599,526 B2 | 7/2003 | Dimitrijevich | |
| 7,318,998 B2 * | 1/2008 | Goldstein | A61L 27/3604 128/898 |
| 8,828,043 B2 * | 9/2014 | Chambers | A61B 17/12122 606/200 |
| 8,921,583 B2 * | 12/2014 | Phiasivongsa | C07D 303/36 549/512 |
| 2001/0053839 A1 | 12/2001 | Noishiki | |
| 2003/0003157 A1 * | 1/2003 | Ohan | A61L 15/325 424/499 |
| 2003/0187515 A1 | 10/2003 | Hariri | |
| 2003/0225355 A1 | 12/2003 | Butler | |
| 2003/0235580 A1 * | 12/2003 | Zhang | A61K 35/50 424/130.1 |
| 2004/0048796 A1 | 3/2004 | Hariri | |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |
| 2008/0131522 A1 | 6/2008 | Liu | |
| 2008/0193554 A1 | 8/2008 | Dua | |
| 2008/0274184 A1 | 11/2008 | Hunt | |
| 2009/0208551 A1 | 8/2009 | Kim | |
| 2010/0104539 A1 | 4/2010 | Daniel et al. | |
| 2010/0106233 A1 | 4/2010 | Grant et al. | |
| 2011/0129520 A1 | 6/2011 | Bogdansky | |
| 2011/0189301 A1 | 8/2011 | Yang | |
| 2011/0307003 A1 * | 12/2011 | Chambers | A61B 17/12122 606/200 |
| 2012/0009644 A1 | 1/2012 | Hamby et al. | |
| 2012/0009679 A1 | 1/2012 | Hamby et al. | |
| 2012/0078378 A1 * | 3/2012 | Daniel | A61L 27/3604 623/23.72 |
| 2012/0083900 A1 | 4/2012 | Samaniego et al. | |
| 2013/0202676 A1 * | 8/2013 | Koob | A61L 27/3604 424/443 |
| 2013/0344162 A1 * | 12/2013 | Morse | A61K 35/50 424/582 |

FOREIGN PATENT DOCUMENTS

| | | | |
|---|---|---|---|
| EP | 0781564 A2 | | 7/1997 |
| WO | 2009044408 A1 | | 4/2009 |
| WO | WO 2009/044408 | * | 9/2009 |
| WO | 2012003377 A2 | | 1/2012 |
| WO | 2012112417 A2 | | 8/2012 |
| WO | 2012112441 A1 | | 8/2012 |

OTHER PUBLICATIONS

Difference Between Amnion and Chorion; Celine. DifferenceBetween.net Online, URL < http://www.differencebetween.net/science/health/difference-between-amnion-and-chorion/> 2011, 7 pages.*

Cargnoni et al. Amniotic Membrane Patching Promotes Ischemic Rat Heart Repair; Cell Transplantation, vol. 18, pp. 1147-1159 (2009).*

* cited by examiner

Primary Examiner — Chris R Tate
Assistant Examiner — Douglas F White
(74) Attorney, Agent, or Firm — Brinks Gilson & Lione

(57) ABSTRACT

A cardiothoracic construct fabricated from human birth tissue comprising at least one cross-linked amniotic membrane, or at least one cross-linked chorionic membrane, or at least one amniotic membrane, or at least one chorionic membrane, or any combination thereof wherein the membrane(s) is/are treated with at least one alcohol composition followed by terminal sterilization is provided. Methods of processing a membrane to form a cardiothoracic construct and methods of preventing adhesion after a cardiac surgical procedure are also provided.

18 Claims, 3 Drawing Sheets

CARDIOTHORACIC CONSTRUCT AND METHODS OF USE

CROSS-REFERENCE TO RELATED APPLICATIONS

This application claims priority to U.S. Provisional Patent Application No. 61/802,439 filed Mar. 16, 2013, the contents of which is incorporated herein in its entirety.

FIELD OF THE INVENTION

The present invention is directed to a cardiothoracic construct composed of aseptically recovered human birth tissue, as well as methods of processing the same to prepare a cardiothoracic construct and methods of using the same.

BACKGROUND OF THE INVENTION

During cardiac surgery, access to the coronary vasculature and the heart requires incision through the pericardial sac (i.e., pericardium), which envelops and isolates the heart from the chest walls and surrounding internal organs (e.g. lungs). As a direct result of the surgical trauma, fibrin networks connect apposing tissue surfaces and form extensive, dense and cohesive post-operative fibrous adhesions. Adhesion formation between the heart and the sternum after cardiac surgery places the heart at risk of catastrophic injury during re-entry for a subsequent procedure.

For example, a pericardial window is a common cardiac surgical procedure whereby the surgeon creates a fistula (or "window") between the pericardial space and the pleural cavity to allow drainage of pericardial effusion (commonly known as "fluid around the heart"). An untreated pericardial effusion can lead to cardiac tamponade and death. A pericardial window involves the excision of a portion of the pericardium, which allows for the continuous draining of the pericardial effusion to the peritoneum or chest cavity, where the fluid is not as dangerous. Once the surgery is complete, the chest cavity is closed, but the incision in the pericardium may be loosely closed or left open. In either case, due to post-surgical edema, the incision usually becomes an oval opening. During the healing process, the flaps of the pericardium adhere to ("scar down") the chest wall, lungs, epicardium and other adjacent tissues and organs, creating post-operative fibrous adhesions.

To gain access to the coronary vasculature and the heart, a surgeon may perform a median sternotomy. During a sternotomy, a vertical inline incision is made along the sternum and the sternum itself is subsequently divided. Such a procedure results in trauma in and around the tissue surrounding the sternum putting the patient at risk for complications arising from slow or impaired sternal wound healing. Sternal nonunion as the result of cardiac intervention or trauma remains a morbid condition with serious sequelae. Furthermore, adhesion formation after cardiac surgery is a well-documented, significant complication encountered during secondary procedures. Adhesion removal, while essential, is a tedious and risky process that can increase the time of an operation by 60 minutes or more. Sternal re-entry and dissection of post-operative cardiac adhesions can expose a patient to critical risks, such as injury to the innominate vein and aorto-coronary bypass grafts. Prevention of adhesions and the treatment of surgical sites remain a challenge. In recent years, bioresorbable anti-adhesion barriers have replaced non-biodegradable synthetic materials (e.g., fine surgical steel wire mesh). However, there remains a need in the art for a safe, effective means of adhesion prevention in an around the pericardium and heart after cardiac surgery using a human birth tissue construct as well as a safe, effective means of wound healing and adhesion prevention in an around surgical sites such as those resulting from a pericardial window or median sternotomy.

SUMMARY OF THE INVENTION

The present invention is generally directed to a cardiothoracic construct and processes for producing the cardiothoracic construct. The cardiothoracic construct of the present invention has unique properties that prevent adhesion formation, reduce or prevent clot formation, prevent fibrous scar formation, and reduce pain and inflammation after application.

According to one aspect, a cardiothoracic construct is provided that includes at least one cross-linked amniotic membrane, or at least one cross-linked chorionic membrane, or at least one amniotic membrane, or at least one chorionic membrane, or a combination thereof. The cross-linked membrane(s) are treated with a cross-linking solution comprising from about 0.05% to about 3% glutaraldehyde. The membrane(s) is/are treated with at least one alcohol composition followed by terminal sterilization to form a cardiothoracic construct. The alcohol composition comprises from about 90% to about 100% ethanol. Terminal sterilization is carried out via gamma irradiation or electron beam irradiation.

According to another aspect, a method of preparing a membrane for a cardiothoracic construct is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) covering the membrane with a substrate on both the fetal membrane side and the maternal membrane side;

(f) optionally, immersing the membrane in a preservative solution for a period of up to about 20 minutes, wherein the preservative solution comprises from about 0.05% to about 3% glutaraldehyde, an alcohol composition or a combination thereof;

(g) optionally, rinsing the membrane with a sterile saline solution;

(h) optionally, soaking the membrane in a sterile saline solution;

(i) immersing the membrane in an alcohol composition for a period of from about 24 hours to about 384 hours;

(j) removing the substrate from both the fetal membrane side and the maternal membrane side;

(k) spreading the membrane on a flat, dry and sterile surface;

(l) allowing the membrane to air dry completely at ambient temperature for a period of up to three hours;

(m) cutting the membrane to a predetermined size; and (n) placing the fetal side of the membrane directly onto a pre-cut substrate to form a cardiothoracic construct.

The method of preparing a membrane for a cardiothoracic construct may further include the steps of packaging the cardiothoracic construct in a dry state or wet state and terminally sterilizing the packaged cardiothoracic construct using irradiation. According to one embodiment, the method may further include the step of removing the chorionic membrane via blunt dissection and discarding the chorionic membrane. According to another embodiment, the method may further include the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) may include from about 0.9% to about 20% NaCl. According to one embodiment, the sterile saline solution in steps (d) and (g) may also include from about 0.9% to about 20% NaCl. According to one embodiment, the rinse steps (d) and (g) are conducted for a maximum time period of five minutes. According to one embodiment, the sterile saline solution in step (h) comprises from about 0.9% to about 20% NaCl, and the soak in step (h) is conducted for a maximum period of about 35 minutes. According to one embodiment, the preservative solution comprises 0.1% glutaraldehyde. According to one embodiment, the alcohol composition in steps (f) and (i) each include from about 90% to about 100% ethanol. According to another embodiment, the alcohol composition in steps (f) and (i) comprises 95.5% ethanol. According to another embodiment, the alcohol composition in steps (f) and (i) comprises 100% ethanol. According to one embodiment, the method further includes the step of treating the membrane with an oxidizer between steps (a) and (b). According to one embodiment, the oxidizer is hydrogen peroxide and the step of treating the membrane further includes the steps of:

(a) rinsing the membrane with about 120 ml of sterile isotonic solution per gram of membrane for a time period of up to about ten minutes;

(b) treating the membrane with about 60 ml of hydrogen peroxide per gram of membrane for a time period of up to about ten minutes; and (c) rinsing the membrane with about 120 ml of sterile isotonic solution per gram of membrane for a time period of up to about ten minutes.

According to another aspect, a cardiothoracic construct is provided that is produced by the aforementioned method. According to one embodiment, the ethanol residual levels determined by gas chromatography are not detected at the corresponding minimum report limit. According to one embodiment, the glutaraldehyde residual levels determined by gas chromatography are not detected at the corresponding minimum reporting limit.

According to another aspect, a method of preventing adhesion at a surgical procedure is provided. The method includes the steps of providing a cardiothoracic construct as provided herein and applying the cardiothoracic construct to the surgical site. According to one embodiment, the surgical site is an incision from a pericardial window procedure. According to one embodiment, the surgical site is the result of a sternotomy procedure.

According to another aspect, a kit for use by a medical professional is provided. According to one embodiment, the kit includes one or more packaged and sterilized cardiothoracic constructs as provided herein. The kit may further include at least one set of instructions.

DETAILED DESCRIPTION OF THE INVENTION

Figure 1:
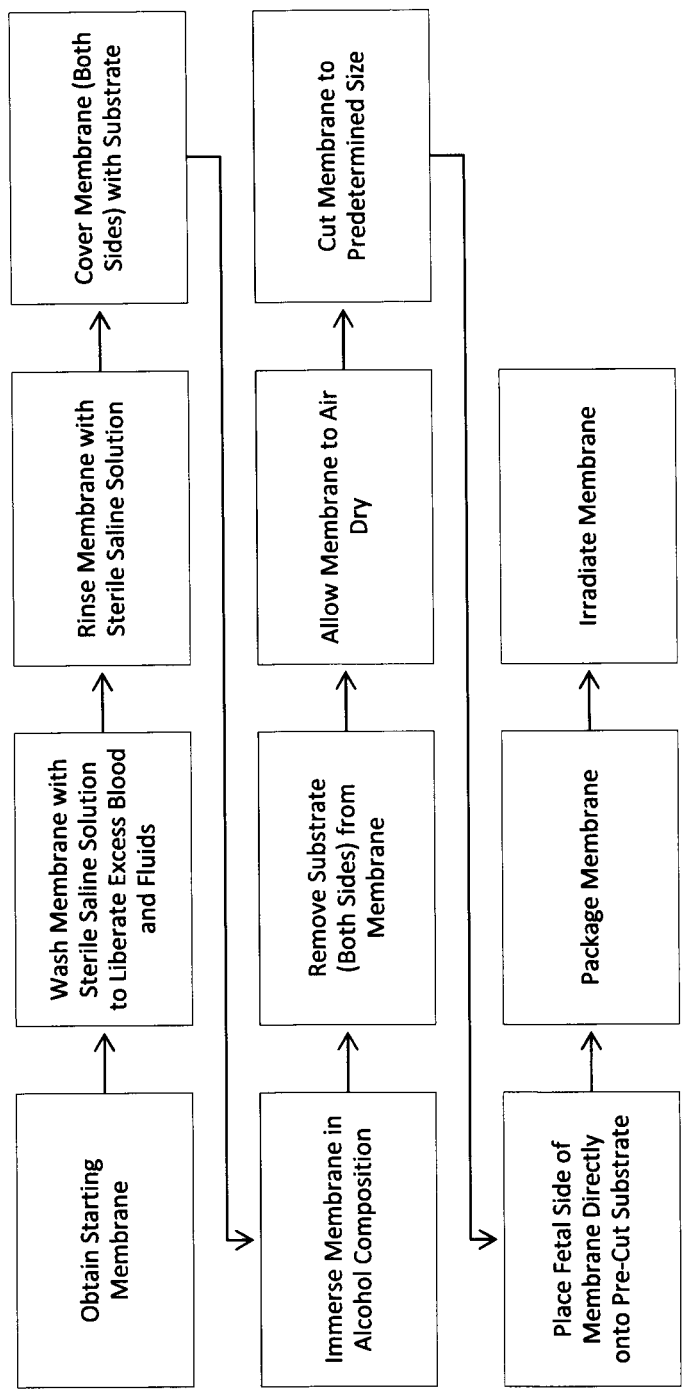
FIG. 1 illustrates a method of preparing a cardiothoracic construct according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

As used herein, the term "human birth tissue" includes, but is not limited to, elements of the placental organ such as, for example, the placental globe, umbilical cord, associated membranes (chorionic membrane and amniotic membrane), and other gelatins, fluids, cells and extracellular material obtained from a seronegative, healthy human.

As used herein, the term "amnion" and "amniotic membrane" are used interchangeably.

As used herein, and in the appended claims, the term "construct" refers to a patch, graft, or other material embodiment suitable for contacting a tissue or organ (e.g., pericardium or heart) and separating it from surrounding tissues and organs.

The present invention generally relates to the use of at least one cross-linked amniotic membrane, or at least one cross-linked chorionic membrane, or at least one amniotic membrane, or at least one chorionic membrane, or a combination thereof, wherein the membrane(s) is/are treated with at least one alcohol composition followed by terminal sterilization to form a cardiothoracic construct. In a preferred embodiment, the cardiothoracic construct is a sterile, biocompatible structure that forms a physical barrier between the pericardium and surrounding tissues and organs, thereby preventing adhesion formation. The cardiothoracic construct further aids in the healing cascade by reducing or preventing clot formation, preventing fibrous scar formation, and reducing pain and inflammation after implantation. In certain embodiments, the cardiothoracic construct is fully resorbed by the body after placement. In other embodiments, the cardiothoracic construct remains intact on or around pericardium.

In a preferred embodiment, the cardiothoracic construct is placed over the surface of the heart and/or pericardium at the conclusion of an open heart surgery procedure to minimize the formation of post-operative fibrous adhesions. Once in place, the placental construct acts as a barrier to physically separate apposing surfaces (e.g., tissues and/or organs) to reduce the risk of them becoming connected through the formation of fibrin bands during the early phase of wound healing. By placing the placental construct between the traumatized tissue surfaces, the formation of the interconnecting fibrous bands between adjacent surfaces is blocked, and the development of fibrous adhesions is reduced.

The cardiothoracic construct may be utilized in conjunction with any variety of cardiac surgical procedures for the prevention of adhesions affecting organs/tissues of the thorax (e.g., heart or pericardium). In certain embodiments, the cardiothoracic construct is particularly suited for treatment of an incision or hole in the pericardium that is the result of a surgical procedure or other trauma. In such an embodiment, the cardiothoracic construct seals the incision or hole in the pericardium, as well as prevents adhesions between other tissues/organs and generally aids in the healing cascade. Exemplary cardiac surgical procedures include, but are not limited to, pericardial window, open heart surgery, coronary artery bypass grafting, myocardial revascularization, valve repair/replacement, aneurysm repair, and heart transplant. The invention further relates to methods for aseptically processing amniotic and chorionic membranes to produce a material that may be used to prepare a cardiothoracic construct.

According to an alternative embodiment, the cardiothoracic construct may be applied to the vertical line incision arising from a sternotomy surgical procedure. During such a procedure, after the incision is made, the sternum itself is divided to allow for access to the heart and lungs. The resulting incision may be difficult or slow to heal due to the induced trauma to the skin and surrounding tissue. The cardiothoracic construct as described herein may be applied directly onto or into the incision to aid in healing and prevent adhesions.

According to another embodiment, the cardiothoracic construct as provided herein may be used to coat or otherwise wrap around a heart device to aid in rejection and prevent adhesion upon implantation. Such devices include, but are not limited to, ventricular assist devices.

Cross-linked and non-cross-linked amniotic and chorionic membranes may be utilized alone or in various combinations or layers to form the cardiothoracic construct. The present disclosure provides methods of preparing a cardiothoracic construct that includes at least one cross-linked amniotic membrane, or at least one cross-linked chorionic membrane, or at least one amniotic membrane, or at least one chorionic membrane, or a combination thereof. Thus, the term "membrane" refers to a cross-linked amniotic membrane, a cross-linked chorionic membrane, an amniotic membrane, a chorionic membrane or any combination thereof. According to a preferred embodiment, the resulting membrane(s) is/are treated with at least one alcohol composition and then terminally sterilized to form a cardiothoracic construct.

According to one embodiment, the membrane(s) is/are cross-linked by treating the membrane(s) with a glutaraldehyde composition. The glutaraldehyde composition includes glutaraldehyde typically in an amount from about 0.05% to about 3%. The resulting membrane(s) is/are treated with at least one alcohol composition which includes typically from about 90% to about 100% ethanol and then terminally sterilized to form a cardiothoracic construct.

According to one embodiment, the membrane(s) is/are not cross-linked. The membrane(s) is/are treated with one alcohol composition that include typically from about 90% to about 100% ethanol. According to an alternative embodiment, the membrane(s) is/are treated with at least two alcohol compositions that each include typically from about 90% to about 100% ethanol. The resulting membrane(s) is/are terminally sterilized to form a cardiothoracic construct.

In certain embodiments, the cardiothoracic construct is formed as a solid construct and may be of various physical sizes, thickness, and shapes. According to such an embodiment, the cardiothoracic construct is preferably of sufficient size and shape to be applied onto or around the pericardium or heart. The cardiothoracic construct thickness may vary depending on the type(s) of membrane used, number of membrane layers, and the type of surgical procedure.

To obtain the human birth tissue material needed to prepare a cardiothoracic construct, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc-total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), and other gelatins, fluids, cells and extracellular matrix can be recovered from a seronegative, healthy human after the newborn is removed. The placental globe, umbilical cord, and other gelatins, fluids, cells and extracellular matrix can be removed and discarded.

The membrane giving rise to the cardiothoracic construct as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane may be identified to ensure that in use a particular side of the membrane is applied at a specific site within the body. Either the fetal side or the maternal side of the membrane may be used depending upon the specific use or procedure that is being performed.

Figure 2:
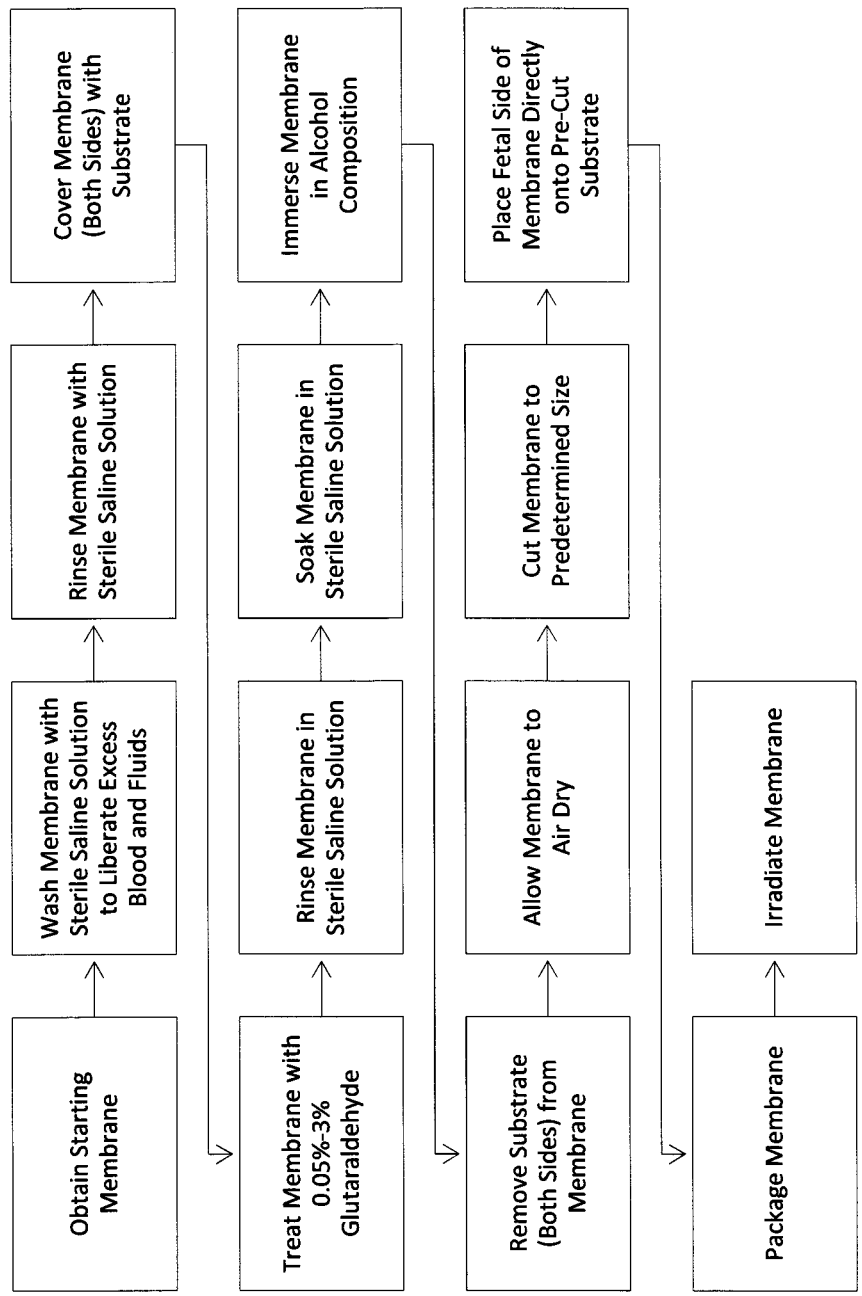
FIG. 2 illustrates a method of preparing a cardiothoracic construct according to one embodiment.
Figure 3:
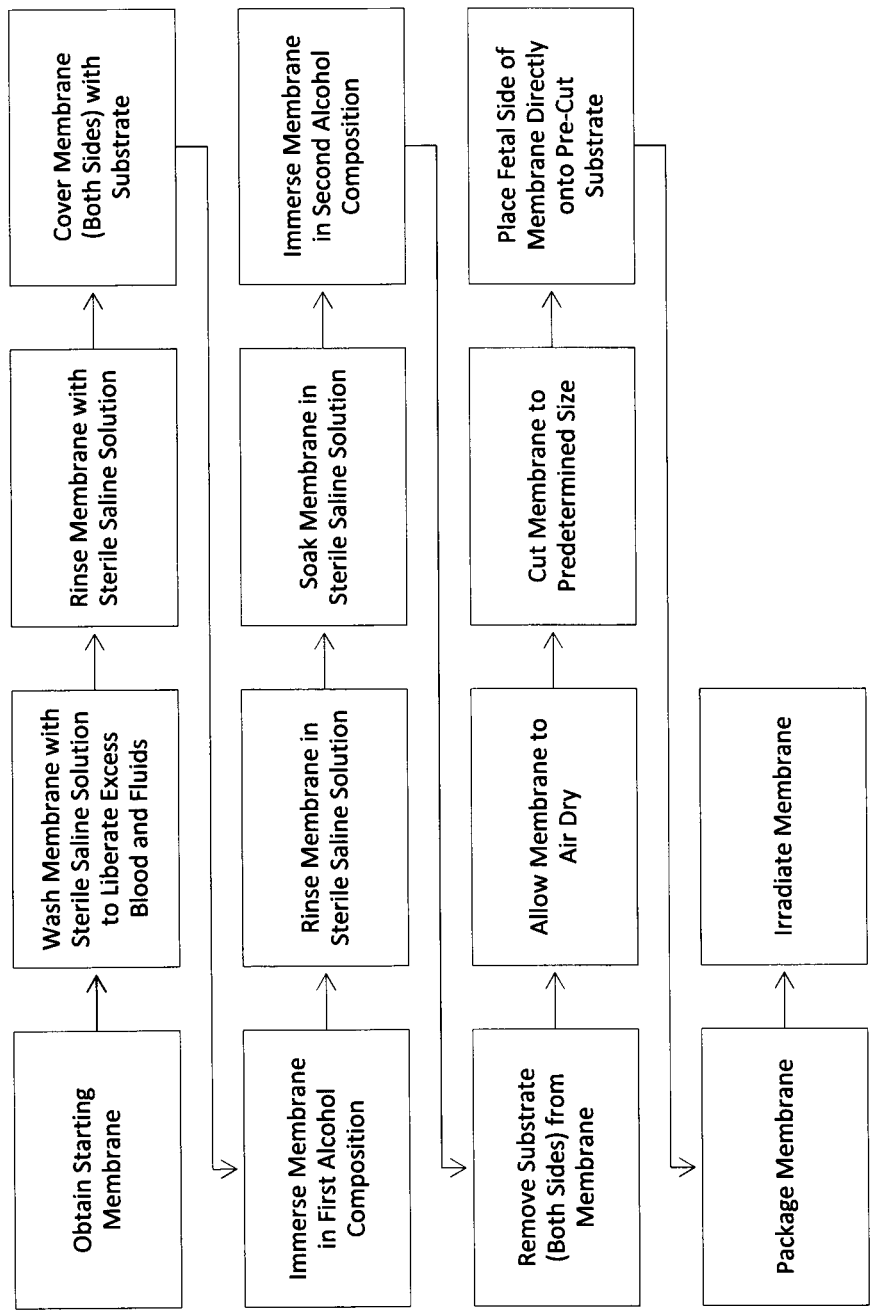
FIG. 3 illustrates a method of preparing a cardiothoracic construct according to one embodiment.

According to the embodiment as illustrated in FIG. 1, FIG. 2 or FIG. 3, the cardiothoracic construct is prepared by first obtaining amniotic membrane, chorionic membrane, or both amniotic and chorionic membrane from a seronegative, healthy human via cesarean section or vaginal delivery as described herein. In particular embodiments where only the amniotic membrane is chosen for further processing, the chorionic membrane can be removed by blunt dissection.

For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about 120 hours prior to further processing. According to one embodiment, the sterile saline solution comprises from about 0.9% to about 20% NaCl, preferably 15% NaCl.

Optionally, the membrane may be treated with an oxidizer. In one embodiment, the oxidizer is hydrogen peroxide, which is also used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution.

According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is covered with a substrate on both the fetal membrane side and the maternal membrane side. Appropriate substrates include, but are not limited to, a sterile mesh or polymer mesh of adequate size and shape for covering each side of the membrane.

According to the embodiment as illustrated in FIG. 2, the membrane is then optionally immersed in a preservative solution for a period of time of typically up to about twenty minutes. The preservative solution includes typically from about 0.05% to about 3% glutaraldehyde and, preferably, about 0.1% glutaraldehyde. The membrane may then be optionally stirred or swirled at a temperature of typically about 22° C. (±1-5° C.). When present, glutaraldehyde leads to collagen cross-linking, which, in turn, leads to a significant increase in the biomechanical strength of the membrane. Additionally, the handling characteristics of the membrane are improved after glutaraldehyde treatment because the membrane is more rigid and does not fold over onto itself. Glutaraldehyde cross-linking also prohibits fast resorption of the membrane by the body after implantation. The glutaraldehyde treatment is preferably performed in a bowl or tray of sufficient size to allow the membrane to spread out in order to maximize exposure of the tissue to the glutaraldehyde solution. Sufficient glutaraldehyde solution should be used to immerse the membrane in the solution. Typically, a minimum of about 400 ml of glutaraldehyde solution is used.

According to the alternative embodiment as illustrated in FIG. 3, the preservative solution may optionally include from about 90% to about 100% ethanol (i.e., in the absence of glutaraldehyde (see FIG. 3—referred to as "first alcohol composition")). In certain embodiments, the alcohol composition includes about 95.5% ethanol. In other embodiments, the alcohol composition includes about 100% ethanol. A cardiothoracic construct produced according to the embodiment of FIG. 3 will be resorbed more quickly by the body (as opposed to gluteraldehyde treatment followed by alcohol treatment).

As illustrated in the embodiments of FIGS. 2 and 3, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1, 2, and 3, the membrane is then immersed in an alcohol composition for a period of typically from about 24 hours to about 384 hours. The alcohol composition includes about 90% to about 100% ethanol. In certain embodiments, the alcohol composition includes about 95.5% ethanol. In other embodiments, the alcohol composition includes about 100% ethanol. Treatment of the membrane within a particular alcohol concentration range for the particular timeframe at this step in the process has yielded unexpected results related to the handling characteristics. One of ordinary skill in the art appreciates the difficulty of handling and manipulating amniotic and chorionic tissue during manipulation and application. Specifically, existing amniotic and chorionic grafts are difficult to place over or around a specific site, particularly because these grafts fold back over on themselves ("wrinkling"), rendering proper placement and positioning very challenging. When treated with the aforementioned alcohol composition for the particular timeframe, the resulting cardiothoracic construct experiences further cross-linking which aids in the handling characteristics of the cardiothoracic construct. The alcohol-treated membrane does not "wrinkle" and allows for ease of application to a specific site. Furthermore, the alcohol treatment is multifunctional, providing a means of sterilization, preservation, and chemical dehydration for the graft, in addition to serving as a radioprotectant for the graft prior to terminal irradiation.

The substrate can then be removed from both the fetal membrane side and the maternal membrane side. The alcohol-treated membrane can then be spread on a flat, dry and sterile surface. The membrane is then allowed to air dry completely at ambient temperature for a period of up to typically about three hours. The membrane can then be cut to the desired size, covered with a substrate, and subsequently packaged. In certain embodiments, the cardiothoracic construct can be cut into patches of any desired size for a particular application by a rotary type cutting tool. A grooved or similarly indicated cutting board may be used to aid in cutting a straight and correctly sized covering. In another embodiment, the cardiothoracic construct is cut by free hand using a scalpel and ruler to achieve the desired size. The fetal side of the membrane can then be placed directly onto a pre-cut substrate to form a cardiothoracic construct. Suitable substrates include, for example, a gauze or synthetic mesh. In certain embodiments, the cardiothoracic construct is packaged in a dry state. In other embodiments, the cardiothoracic construct is packaged in a wet state, including, but not limited to, sterile water, crystalloids, ethanol, or another sterilizing, preserving or storage agent. The covering can be removed after the opposing side has been applied to the chosen site. The packaging and covering as disclosed herein can facilitate the handling of the cardiothoracic construct, namely maintaining and identifying the orientation of the fetal and maternal side of the cardiothoracic construct for the user. The packaging may also promote storage of the cardiothoracic construct.

The packaged cardiothoracic construct can be terminally sterilized using irradiation. In one embodiment, an electron beam irradiation is applied in an amount up to about 45 kGy. The sterilized cardiothoracic construct may be stored for up to typically about two years from the date of processing. In one embodiment, the cardiothoracic construct may be stored under proper conditions for as much as about five years following processing. According to a preferred embodiment, the cardiothoracic construct may be stored under proper conditions for two years following processing. The sterilized cardiothoracic construct may be stored in any container suitable for long-term storage. Preferably, the sterilized cardiothoracic construct is stored in a sterile double peel-pouch package.

If desired, the membrane may be treated to provide for the delivery of a variety of antibiotics, anti-inflammatory agents, growth factors and/or other specialized proteins or small molecules that assist in the healing cascade after cardiac surgery. In addition, the membrane may be combined with a substrate (sterile gauze, sterile polymer material or other tissue or biomaterial) to increase the strength of the cardiothoracic construct.

A method of preventing adhesion after a cardiac surgical procedure is also provided. The method includes the steps of providing a cardiothoracic construct as provided herein and applying the cardiothoracic construct to the surgical site. According to one embodiment, the surgical site is the result of a variety of cardiac surgical procedures for the treatment of diseases affecting organs/tissues inside the thorax (e.g., heart or pericardium). Exemplary cardiac surgical procedures include pericardial window procedure, open heart surgery, coronary artery bypass grafting, myocardial revascularization, valve repair/replacement, aneurysm repair, and heart transplant.

According to an alternative embodiment, the surgical site is an incision arising from a cardiothoracic surgery such as a sternotomy. According to such an embodiment, the surgical site may be treated with a cardiothoracic construct as provided herein.

If desired, the one or more membranes forming the cardiothoracic construct(s) may be utilized with at least one composition or device for delivering, fastening or fixing the cardiothoracic construct(s) on or around a specific site. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures or forceps.

A kit for use by a medical professional is also provided. According to one embodiment, the kit includes one or more packaged and sterilized cardiothoracic constructs as provided herein and at least one set of instructions. The kit may further include at least one composition or device for delivering, fastening or fixing the cardiothoracic construct in place at a particular site. The kit may further include a container adapted to accommodate the aforementioned components while preserving the cardiothoracic construct as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1

Representative samples of final product from four production lots #1, #2, #3 and #4 manufactured according to the methods of FIG. 2 were tested for residual glutaraldehyde and residual ethanol by gas chromatography, analytical methods EPA 8015M, CAS No. 111-30-8 and EPA 8260B, CAS No. 64-17-5, respectively. Samples were sent to Nelson Laboratories, Inc., 6280 South Redwood Road Salt Lake City, Utah 84123, a GLP qualified microbiology laboratory registered with the FDA and third-party accredited to ISO 17025 standards. The results are summarized in Table 1 and Table 2 below.

Samples from four production lots #1, #2, #3 and #4 were tested for residual glutaraldehyde by gas chromatography, analytical methods EPA 8015M, CAS No. 111-30-8 as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.046 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.051 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #2.

Two representative samples of final product (2 cm×6 cm each) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.069 g and a fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #3.

One sample of final product (4 cm×4 cm) from production lot #4 included an amniotic membrane that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, one test article was extracted with a weight of 0.037 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #4.

Samples from the same four production lots #1, #2, #3 and #4 were tested for residual ethanol by gas chromatography, analytical method EPA 8260B, CAS No. 64-17-5, as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.05 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.04 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #2.

Two samples of final product (4 cm×4 cm and 2 cm×6 cm) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.08 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #3.

Two samples of final product (4 cm×4 cm each) from production lot #4 included amniotic membranes that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, the two samples were pooled, and a test article was extracted with a weight of 0.09 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #4.

TABLE 1

Glutaraldehyde Determination for Production Lots #1, #2, #3 and #4

| Production Lot | Total Time in Glutaraldehyde | Weight of Sample | Volume of Fluid | Starting Extraction Temperature | Ending Extraction Temperature | Duration of Extraction | Sample Results |
|---|---|---|---|---|---|---|---|
| 1 | 15 Minutes | 0.046 g | 100mL | 22° C. | 23° C. | 24 Hours | ND* |
| 2 | 15 Minutes | 0.051 g | 100mL | 22° C. | 23° C. | 24 Hours | ND* |
| 3 | 15 Minutes | 0.069 g | 100mL | 22° C. | 23° C. | 24 Hours | ND* |
| 4 | 15 Minutes | 0.037 g | 100mL | 22° C. | 23° C. | 24 Hours | ND* |

*ND = Not Detected at the Minimum Reporting Limit (1.0 mg/L)

TABLE 2

Ethanol Determination for Production Lots #1, #2, #3 and #4

| Production Lot | Total Time in Etanol | Weight of Sample | Volume of Fluid | Starting Extraction Temperature | Ending Extraction Temperature | Duration of Extraction | Sample Results |
|---|---|---|---|---|---|---|---|
| 1 | 24.0 Hours | 0.05 g | 50 mL | 22° C. | 23° C. | 24 Hours | ND* |
| 2 | 24.1 Hours | 0.04 g | 50 mL | 22° C. | 23° C. | 24 Hours | ND* |
| 3 | 41.3 Hours | 0.08 g | 50 mL | 22° C. | 23° C. | 24 Hours | ND* |
| 4 | 114.7 Hours | 0.09 g | 50 mL | 22° C. | 23° C. | 24 Hours | ND* |

*ND = Not Detected at the Minimum Reporting Limit (0.5 mg/L)

Example 2

Three representative samples of final product for each of three production lots manufactured according to the methods of FIG. 1 were tested for residual ethanol by gas chromatography, analytical method EPA 8260B, CAS No. 64-17-5. Samples were sent to Nelson Laboratories, Inc., 6280 South Redwood Road Salt Lake City, Utah 84123, a GLP qualified microbiology laboratory registered with the FDA and third-party accredited to ISO 17025 standards.

The three samples submitted for testing from production lot #5 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #6 (2 cm×3 cm each) included amniotic membranes that had been immersed in an alcohol composition comprising 95.5% ethanol for a period of 25.5 hours. The three samples submitted for testing from production lot #7 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours. All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #5, #6 and #7 indicated no detectable amounts of ethanol at the minimum reporting limit (0.5 mg/L). The results are summarized in Table 3 below.

TABLE 3

Ethanol Determination for Production Lots #5, #6, and #7

| Production Lot | Total Time in Etanol | Weight of Sample | Volume of Fluid | Starting Extraction Temperature | Ending Extraction Temperature | Duration of Extraction | Sample Results |
|---|---|---|---|---|---|---|---|
| 5 | 110.0 Hours | 0.05 g | 50 mL | 22° C. | 23° C. | 24 Hours | ND* |
| 6 | 25.5 Hours | 0.04 g | 50 mL | 22° C. | 23° C. | 24 Hours | ND* |
| 7 | 24.9 Hours | 0.08 g | 50 mL | 22° C. | 23° C. | 24 Hours | ND* |

*ND = Not Detected at the Minimum Reporting Limit (0.5 mg/L)

I claim:

1. A method of preventing adhesion at a cardiac surgical site, comprising the steps of:
   providing a cardiothoracic construct; and
   applying the cardiothoracic construct to the surgical site, wherein the cardiothoracic construct is prepared by a process comprising the steps of:
   recovering an amniotic membrane from a human;
   immersing the membrane in an about 0.1% glutaraldehyde solution for about 15 minutes to form a cross-linked amniotic membrane;
   immersing the cross-linked membrane with one alcohol composition comprising from about 90% to about 100% ethanol for about 24 hours to about 384 hours to chemically dehydrate the cross-linked membrane to form a cardiothoracic construct; and
   terminally sterilizing the cardiothoracic construct with gamma or electron beam irradiation.

2. The method of claim 1, wherein the surgical site is the result of a sternotomy procedure.

3. The method of claim 1, wherein the cardiothoracic construct prevents fibrin band formation with surrounding tissue or organs.

4. The method of claim 1, wherein the cardiothoracic construct is resorbed by the body after application.

5. The method of claim 1, wherein the surgical site arises as a result of a surgical procedure selected from the group consisting of open heart surgery, coronary artery bypass grafting, myocardial revascularization, heart valve repair or replacement, aneurysm repair, and heart transplant.

6. The method of claim 1, wherein the cardiothoracic construct is secured to the surgical site using a composition selected from the group consisting of sutures, tissue glue, tissue adhesive, fibrin glue, fibrinogen glue, hydrogel tissue glue, chondroitin sulfate aldehyde, and natural proteins.

7. The method of claim 1, wherein the surgical site is an incision in the pericardium from a pericardial window procedure.

8. The method of claim 7, wherein the cardiothoracic construct is placed directly on a heart surface, pericardium surface, or both.

9. The method of claim 1, further comprising the step of packaging the cardiothoracic construct prior to terminally sterilization.

10. The method of claim 9, wherein the cardiothoracic construct is packaged in a wet state.

11. The method of claim 9, wherein the cardiothoracic construct is packaged in a dry state.

12. A method of preventing adhesion at a cardiac surgical site, comprising the steps of:
   recovering an amniotic membrane from a human;
   immersing the membrane in an about 0.1% glutaraldehyde solution for about 15 minutes to form a cross-linked amniotic membrane;
   immersing the cross-linked membrane with one alcohol composition comprising from about 90% to about 100% ethanol for about 24 hours to about 384 hours to chemically dehydrate the cross-linked membrane to form a cardiothoracic construct;
   terminally sterilizing the cardiothoracic construct with gamma or electron beam irradiation; and
   applying the cardiothoracic construct to the surgical site.

13. The method of claim 12, wherein the surgical site is an incision in the pericardium from a pericardial window procedure.

14. The method of claim 12, wherein the surgical site is the result of a sternotomy procedure.

15. The method of claim 12, wherein the cardiothoracic construct prevents fibrin band formation with surrounding tissue or organs.

16. The method of claim 12, wherein the cardiothoracic construct is resorbed by the body after application.

17. The method of claim 12, wherein the cardiothoracic construct is placed directly on a heart surface, pericardium surface, or both.

18. The method of claim 12, wherein the surgical site arises as a result of a surgical procedure selected from the group consisting of open heart surgery, coronary artery bypass grafting, myocardial revascularization, heart valve repair or replacement, aneurysm repair, and heart transplant.

\* \* \* \* \*